(12) United States Patent
Zhu et al.

(10) Patent No.: US 11,603,537 B2
(45) Date of Patent: Mar. 14, 2023

(54) METHOD FOR IMPROVING RICE YIELD BY JOINTLY KNOCKING OUT ABA RECEPTOR PYL FAMILY GENES AND USE THEREOF

(71) Applicant: Shanghai Institutes For Biological Sciences, Chinese Academy Of Sciences, Shanghai (CN)

(72) Inventors: Jiankang Zhu, Shanghai (CN); Chunbo Miao, Shanghai (CN)

(73) Assignee: CAS Center for Excellence in Molecular Plant Sciences, Shanghai (CN)

( * ) Notice: Subject to any disclaimer, the term of this patent is extended or adjusted under 35 U.S.C. 154(b) by 0 days.

(21) Appl. No.: 16/652,391

(22) PCT Filed: Sep. 30, 2018

(86) PCT No.: PCT/CN2018/109061
§ 371 (c)(1),
(2) Date: Mar. 30, 2020

(87) PCT Pub. No.: WO2019/063009
PCT Pub. Date: Apr. 4, 2019

(65) Prior Publication Data
US 2020/0283785 A1    Sep. 10, 2020
US 2021/0261977 A9    Aug. 26, 2021

(30) Foreign Application Priority Data
Sep. 30, 2017  (CN) .......................... 201710917637.0

(51) Int. Cl.
*C12N 15/82*  (2006.01)
*A01H 1/04*   (2006.01)
*A01H 4/00*   (2006.01)
*C12N 9/22*   (2006.01)

(52) U.S. Cl.
CPC .......... *C12N 15/8261* (2013.01); *A01H 1/04* (2013.01); *A01H 4/008* (2013.01); *C12N 9/22* (2013.01); *C12N 15/8201* (2013.01); *C12N 2310/20* (2017.05)

(58) Field of Classification Search
None
See application file for complete search history.

(56) References Cited

FOREIGN PATENT DOCUMENTS

| CN | 104170823 A | 12/2014 | | |
|----|-------------|---------|---|---|
| CN | 107207573 A | 9/2017 | | |
| WO | WO-2016033230 A1 | * | 3/2016 | ........... C07K 14/415 |
| WO | WO 2017165855 A2 | 9/2017 | | |

OTHER PUBLICATIONS

Doerks et al., (TIG, 14:248-250, 1998).*
Smith et al. (Nature Biotechnology, 15:1222-1223, 1997).*
Bork et al. (TIG, 12:425-427, 1996).*
Tian et al. (Rice, 8:28, 1-13, 2015).*
Yu et al. (Front. Plant Sci. 8:1752, pp. 1-13; 2017).*
Gutterson (HortScience 30:964-966,1995).*
Bruening (Proc. Natl. Acad. Sci., 95:13349-13351, 1998).*
Elomaa et al. (Molecular Breeding, 2:41-50, 1996).*
Colliver et al. (Plant molecular Biology, 35:509-522, 1997).*
Emery et al. (Current Biology 13:1768-1774, 2003).*
Arziman et al. (Nucleic Acids Research, 33:582-588, 2005).*
Bonawitz et al.,(Annu. Rev. Genet. 44: 337-363, 2010).*
Paul et al. (Plant Cell Reports; 35:1417-1427; 2016).*
International Search Report and Written Opinion for Application No. PCT/CN2018/109061, dated Dec. 10, 2018.
International Preliminary Report on Patentability for Application No. PCT/CN2018/109061, dated Apr. 9, 2020.
Feng et al., Plant Abscisic Acid Receptors PYR/PYL/RCAR. Chemistry of Life. Dec. 2015:35(6):721-726. doi: 10.13488/j.smhx.20150604.
Gonzalez-Guzman et al., *Arabidopsis* PYR/PYL/RCAR receptors play a major role in quantitative regulation of stomatai aperture and transcriptional response to abscisic acid. Plant Cell. Jun. 2012;24(6):2483-96. doi: 10.1105/tpc.112.098574. Epub Jun. 26, 2012.

* cited by examiner

*Primary Examiner* — Vinod Kumar
(74) *Attorney, Agent, or Firm* — Wolf, Greenfield & Sacks, P.C.

(57) ABSTRACT

Provided are a method for improving rice yield by jointly knocking out ABA receptor PYL family genes and a use thereof.

4 Claims, 6 Drawing Sheets
Specification includes a Sequence Listing.

SEQUENCE LISTING

<160> NUMBER OF SEQ ID NOS: 21

<210> SEQ ID NO 1
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 1
tcagcttccg cgtcgtcggc gg                                              22

<210> SEQ ID NO 2
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 2
gcgcaccacc gctacgccgt ggg                                             23

<210> SEQ ID NO 3
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 3
ggcggcggta aggcgtgccc gg                                              22

<210> SEQ ID NO 4
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 4
ggatcattgg aggtgaccat agg                                             23

<210> SEQ ID NO 5
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 5
agcggcaggg aagttgccaa tgg                                             23

<210> SEQ ID NO 6
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 6
ccgggaggag gagatggagt ac                                              22

<210> SEQ ID NO 7
<211> LENGTH: 23
<212> TYPE: DNA
<213> ORGANISM: Artificial Sequence

```
<220> FEATURE:
<223> OTHER INFORMATION: Synthetic Polynucleotide

<400> SEQUENCE: 7
ggtggcggct ggcggacgag agg                                              23

<210> SEQ ID NO 8
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 8
gaggaggagg ttggagggtc ggg                                              23

<210> SEQ ID NO 9
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 9
gcgcaccacc gctacgccgt ggg                                              23

<210> SEQ ID NO 10
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 10
ccatcgtgcg cagcttcggc aac                                              23

<210> SEQ ID NO 11
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 11
gcgggttcgc caacccgcag cgg                                              23

<210> SEQ ID NO 12
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 12
gtgctcagct tccggatcgt cgg                                              23

<210> SEQ ID NO 13
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 13
gtgtgagata agagcgtggt ggg                                              23
```

<210> SEQ ID NO 14
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 14
ccctggcatc ccgcaccagc acc                                              23

<210> SEQ ID NO 15
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 15
ccgccacgaa atcggtagca acc                                              23

<210> SEQ ID NO 16
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 16
ccggcagttc caccgccacg agc                                              23

<210> SEQ ID NO 17
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 17
ccattataac agaattactc atc                                              23

<210> SEQ ID NO 18
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 18
ggtggcggct ggcggacgag agg                                              23

<210> SEQ ID NO 19
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 19
gaggaggagg ttggagggtc ggg                                              23

<210> SEQ ID NO 20
<211> LENGTH: 23
<212> TYPE: DNA
<213> ORGANISM: Artificial Sequence
<220> FEATURE:
<223> OTHER INFORMATION: Synthetic Polynucleotide

```
<400> SEQUENCE: 20
ggatcattgg aggtgaccat agg                                             23

<210> SEQ ID NO 21
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 21
ccacttggag gtcatcgatg gcc                                             23
```

METHOD FOR IMPROVING RICE YIELD BY JOINTLY KNOCKING OUT ABA RECEPTOR PYL FAMILY GENES AND USE THEREOF

RELATED APPLICATIONS

This application is a national stage filing under 35 U.S.C. § 371 of international application number PCT/CN2018/109061, filed Sep. 30 2018, which claims the benefit of Chinese application number CN 201710917637.0, filed Sep. 30, 2017, the contents of each of which are herein incorporated by reference in their entirety.

TECHNICAL FIELD

The present invention relates to the fields of agriculture and biotechnology, in particular, to a method for improving rice yield by jointly knocking out ABA receptor PYL family genes and uses thereof.

BACKGROUND

Abscisic acid (ABA) is a hormone that can regulate plant growth and enhance plant resistance to stress. Adversity stress, especially drought, can induce the increase of ABA content in plants. Increased ABA content levels will cause widespread and rapid physiological responses in plants, thereby enhancing the plant's resistance to stress. However, this increase in stress resistance is often accompanied by growth inhibition. In plants, ABA is recognized by its receptor proteins PYR/PYL/RCAR (pyrabactin resistance 1/PYR1-like/regulatory components of ABA receptors). The binding of ABA to PYL causes the conformational change of the protein, which causes and promotes the binding of PYL to PP2C (clade A type 2C protein phosphatase) protein. The formation of ABA-PYL-PP2C complex inhibits the activity of PP2C, thereby releasing the activity of SnRK2 (sucrose nonfermenting 1-related protein kinase 2) protein. Activated SnRK2 will phosphorylate many downstream protein factors, causing physiological responses such as the expression of ABA-responsive genes, stomatal closure and germination inhibition.

The PYL protein is encoded by a gene family. There are 13 PYL genes in the rice nuclear genome. Although ABA plays a key role in plant stress resistance and growth regulation, little research has been done on PYL in rice, and the specific gene functions of its family members are unclear. There is no report of rice PYL mutants.

CRISPR/Cas9 technology is a gene editing technology that has emerged in recent years. After its first publication in 2013, the technology was quickly and widely used in gene editing of plants and animals. In this technology system, Cas9 nuclease is guided by short sgRNA (single guide RNA) to cut the DNA sequence complementary to the sgRNA recognition region; expressing multiple sgRNAs in a cell can edit multiple genes at the same time.

SUMMARY OF THE INVENTION

The object of the present invention is to provide a new method for improving rice yield by jointly knocking out ABA receptor PYL family genes.

In a first aspect of the present invention, it provides a method for improving a plant, comprising the steps:
(i) genetically engineering a plant cell or a plant tissue, thereby causing mutations in N members of the PYL gene family, wherein N≥2;
(ii) regenerating the genetically engineered plant cell or plant tissue into a plant and performing a trait testing on a regenerated plant, the trait is selected from the group consisting of: plant height, heading stage, seed dormancy, yield, biomass, and a combination thereof;
(iii) based on the results of the trait testing, selecting a plant with the desired trait characteristics.

In another preferred embodiment, the desired trait characteristics are selected from the group consisting of: increased plant height, increased yield, increased biomass, near-normal seed dormancy, no significant delay in heading stage, and a combination thereof.

In another preferred embodiment, a comprehensive evaluation of plant height, yield, biomass, seed dormancy, and heading stage is performed to select a plant with the desired trait characteristics.

In another preferred embodiment, the desired trait characteristics are selected from the group consisting of: increased biomass, increased yield, near-normal seed dormancy, no significant delay in heading stage, and a combination thereof.

In another preferred embodiment, the mutation includes the reduction of the expression or activity of N members in the PYL gene family.

In another preferred embodiment, the "reduction" refers to reducing the expression or activity of N members in the PYL gene family to meet the following conditions:
the ratio of A1/A0 is ≤80%, preferably ≤60%, more preferably ≤40%, and most preferably 0-30%;
wherein, A1 is the expression or activity of N members in the PYL gene family; A0 is the expression or activity of N members in the same PYL gene family in wild-type plants of the same type.

In another preferred embodiment, the "reduction" means that compared to the expression level E0 of the members of the wild type PYL family, the expression level E1 of the members of the PYL family in the plant is 0-80% of that in the wild type, preferably 0-60%, more preferably 0-40%.

In another preferred embodiment, the reduction of the expression or activity of N members of the PYL gene family in the plant is achieved by a method selected from the group consisting of: gene mutation, gene knockout, gene disruption, RNA interference technology, Crispr technology, and a combination thereof.

In another preferred embodiment, the plant with the desired trait characteristics is selected from the group consisting of: pyl1/4/6 and pyl1/6.

In another preferred embodiment, the plant includes crops, forestry plants, flowers; preferably Gramineae, Leguminosae and Cruciferae plants, and more preferably rice, corn, sorghum, wheat, or soybeans.

In another preferred embodiment, the genetic engineering includes gene editing of members of the PYL gene family with multiple sgRNA-mediated Cas9 nucleases.

In another preferred embodiment, the gene editing includes gene editing of genes selected from the PYL gene family: PYL1, PYL2, PYL3, PYL4, PYL5, PYL6, PYL12, and a combination thereof.

In another preferred embodiment, the gene editing further includes gene editing of genes selected from the PYL gene family: PYL7, PYL8, PYL9, PYL10, PYL11, PYL13, and a combination thereof.

In another preferred example, the gene editing includes gene editing of genes selected from the PYL gene family: PYL1, PYL2, PYL3, PYL4, PYL5, PYL6, PYL7, PYL8, PYL9, PYL10, PYL11, PYL12, PYL13, and a combination thereof.

In a second aspect of the present invention, it provides a genetically engineered plant tissue or plant cell, wherein a mutation occurs in N members of the PYL gene family in a plant tissue or plant cell, wherein N≥2.

In another preferred embodiment, the mutation includes the reduction of the expression or activity of N members in the PYL gene family.

In a third aspect of the present invention, it provides a method for preparing a genetically engineered plant tissue or plant cell, comprising the steps of:

introducing mutations in N members of the PYL gene family in a plant tissue or plant cell to obtain the genetically engineered plant tissue or plant cell, wherein N≥2.

In a fourth aspect of the present invention, it provides a method for preparing a transgenic plant, comprising the steps of:

regenerating the genetically engineered plant tissue or plant cell prepared by the method according to the third aspect of the present invention into a plant, thereby obtaining a transgenic plant.

In a fifth aspect of the present invention, it provides a transgenic plant, which is prepared by the method according to the fourth aspect of the present invention.

In a sixth aspect of the present invention, it provides a method for producing grain, comprising the steps of:

(i) planting a crop in which N members of the PYL gene family are mutated, wherein N≥2;

(ii) harvesting the grain (cereal) of the crop.

In another preferred embodiment, the crop is selected from the group consisting of and comprises Gramineae, Leguminosae and Cruciferae plant, and more preferably rice, corn, sorghum, wheat, and soybeans.

It should be understood that, within the scope of the present invention, the technical features specifically described above and below (such as the Examples) can be combined with each other, thereby constituting a new or preferred technical solution which needs not be described one by one.

DETAILED DESCRIPTION OF INVENTION

Figure 1:
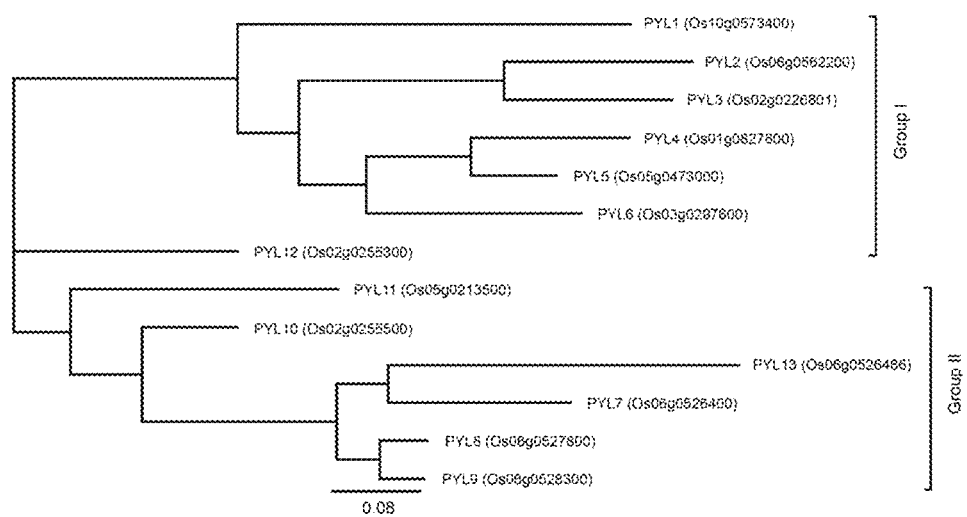
FIG. 1 shows an evolutionary tree analysis of a rice PYL protein sequence. Group I, class I genes; group II, class II genes.

After extensive and intensive research, the inventors has discovered for the first time that knocking out N members (N≥2) of the PYL gene family can dramatically improve certain traits of plants, such as improving the yield of the plant (such as rice). Specifically, the present invention utilizes gene knockout technology (such as CRISPR/Cas9 multi-gene editing technology) for the first time to perform a knockout study of the rice PYL gene, and the inventor has found that knocking out different rice PYL gene family members can promote rice growth or improve some desired agronomic traits, wherein simultaneous knockout of PYL1, PYL4, and PYL6 has shown the best growth status and agronomic traits, which can greatly increase rice yield. On this basis, the present inventors have completed the present invention.

PYL Gene

PYL is an ABA receptor protein coding gene, and PYL exists as a gene family. Existing studies have shown that the genes of the PYL family are highly conserved and are essential for plant growth (especially for stress resistance). The research of the present invention suggests that the modification (such as knockout or down-regulation) of a single PYL gene will not show improvement in plant properties.

In the present invention, N genes (N≥2) of the PYL gene of any plant species can be knocked out. Representative plants include, but are not limited to, forestry plants, agricultural plants, such as Gramineae, Cruciferae, Leguminosae, etc., such as rice, corn, sorghum, wheat, soybeans, and a combination thereof.

It should be understood that different plants may contain multiple PYL genes (i.e., multiple genes from the PYL family). In the present invention, the PYL gene includes all known PYL genes from the plant (or species), PYL genes that might be discovered in the future, and homologous genes that have homology with these PYL genes. Wherein the "having homology" means that the two sequences have an identity of ≥70%, preferably ≥80%, more preferably ≥90%, and most preferably ≥95%.

In other plants, in general, the common name of the homologous genes of the PYL gene is the PYL gene, and the abbreviation of the Latin name of the species may be added before the PYL gene name. For example, wheat PYL gene is also called TaPYL; corn PYL gene is also called ZmPYL; soybean PYL gene is also called GmPYL.

Taking rice as an example, at least 13 PYL genes are known, namely PYL1, PYL2, PYL3, PYL4, PYL5, PYL6, PYL7, PYL8, PYL9, PYL10, PYL11, PYL12, PYL13. In the present invention, two or more PYL genes may be stated in combination, for example, "pyl 1/4/6" means pyl1, pyl4, and pyl6.

In a preferred embodiment, the type of knockout of the rice PYL gene is shown as follows: pyl1/4/6, pyl1/6.

Methods for Improving Plants

In the present invention, a method for improving a plant is also provided, comprising the steps:

(i) genetically engineering a plant cell or a plant tissue, thereby causing mutations in N members of the PYL gene family, wherein N≥2;

(ii) regenerating the genetically engineered plant cell or plant tissue into a plant and performing a trait testing on a regenerated plant, the trait is selected from the group consisting of: plant height, heading stage, seed dormancy, yield, biomass, and a combination thereof;

(iii) based on the results of the trait testing, selecting a plant with the desired trait characteristics.

In the present invention, the mutation includes the reduction of the expression or activity of N members in the PYL gene family.

In a preferred embodiment, the "reduction" refers to reducing the expression or activity of N members in the PYL gene family to meet the following conditions:

the ratio of A1/A0 is ≤80%, preferably ≤60%, more preferably ≤40%, and most preferably 0-30%;

wherein A1 is the expression or activity of N members in the PYL gene family; A0 is the expression or activity of N members in the same PYL gene family in wild-type plants of the same type.

In a preferred embodiment, the "reduction" means that compared to the expression level E0 of the members of the wild type PYL family, the expression level E1 of the members of the PYL family in the plant is 0-80% of that in the wild type, preferably 0-60%, more preferably 0-40%.

In a preferred embodiment, the reduction of the expression or activity of N members of the PYL gene family in the plant is achieved by a method selected from the group consisting of: gene mutation, gene knockout, gene disruption, RNA interference technology, Crispr technology, and a combination thereof.

In the present invention, plants with poor traits are excluded based on the results of the trait test.

In the present invention, it further includes step (iv), further screening the plants having the desired traits selected in step (iii), thereby screening a plant that can balance plant height, yield, biomass, seed dormancy, heading stage, water loss performance and other traits, which shows the best comprehensive traits.

Method for Producing Grain

The present invention also provides a method for producing grain, comprising the steps:

(i) planting a crop in which N members of the PYL gene family are mutated, wherein N≥2;

(ii) harvesting the grain (cereal) of the crop.

The main advantages of the present invention include:

(a) The present invention has found for the first time that knockout of PYL gene family members in different plants (such as rice) can significantly promote plant growth and increase yield.

(b) The present invention has tested for the first time the traits after the knockout of PYL gene family members in different plants (such as rice) and selected plants that have the desired traits (increased biomass, increased yield).

(c) The present invention has found for the first time that plants with simultaneous knockout of PYL1, PYL4, and PYL6 can show the best growth state and agronomic traits, and it can greatly increase rice yield.

The present invention will be further described below with reference to specific embodiments. It should be understood that these examples are only used to illustrate the present invention and not to limit the scope of the present invention. The experimental methods without specific conditions in the following examples are generally based on conventional conditions, such as Sambrook et al., Molecular Cloning: Laboratory Manual (New York: Cold Spring Harbor Laboratory Press, 1989) or Plant Molecular Biology-Experimental Manual (Plant Molecular Biology-A Laboratory Mannual, edited by Melody S. Clark, Springer-verlag Berlin Heidelberg, 1997), or as recommended by the manufacturer.

Unless stated otherwise, percentages and parts are by weight.

Example 1. Multiple Gene Knockout of Members of the Rice PYL Gene Family

To knock out the PYL gene family, we constructed a CRISPR/Cas9 multiple gene knockout system. In this system, Cas9 was mediated and expressed by the maize Ubiquitin promoter; four sgRNAs were mediated and expressed by the OsU3-1, OsU6-1, OsU3-2, and OsU6-2 promoters respectively (for the promoter sequence, see sequence 1 to sequence 4). Four sgRNA expression cassettes are arranged in tandem on the vector. To specifically target the rice PYL gene, we synthesized a primer that specifically recognized the target gene, which contains a 20 bp target recognition sequence and a 4-5 bp tag sequence. Double-stranded DNA with sticky ends was formed after primer annealing (20 bp double-stranded region). The double-stranded DNA was seamlessly linked to the promoter and downstream sequences under the action of T4 ligase, thereby constructing an sgRNA expression cassette. The sgRNA expression cassettes arranged in tandem were firstly constructed in a PUC19 intermediate vector, and then subcloned into a PCAMBIA1300 backbone with Cas9 expression cassette.

Figure 2:
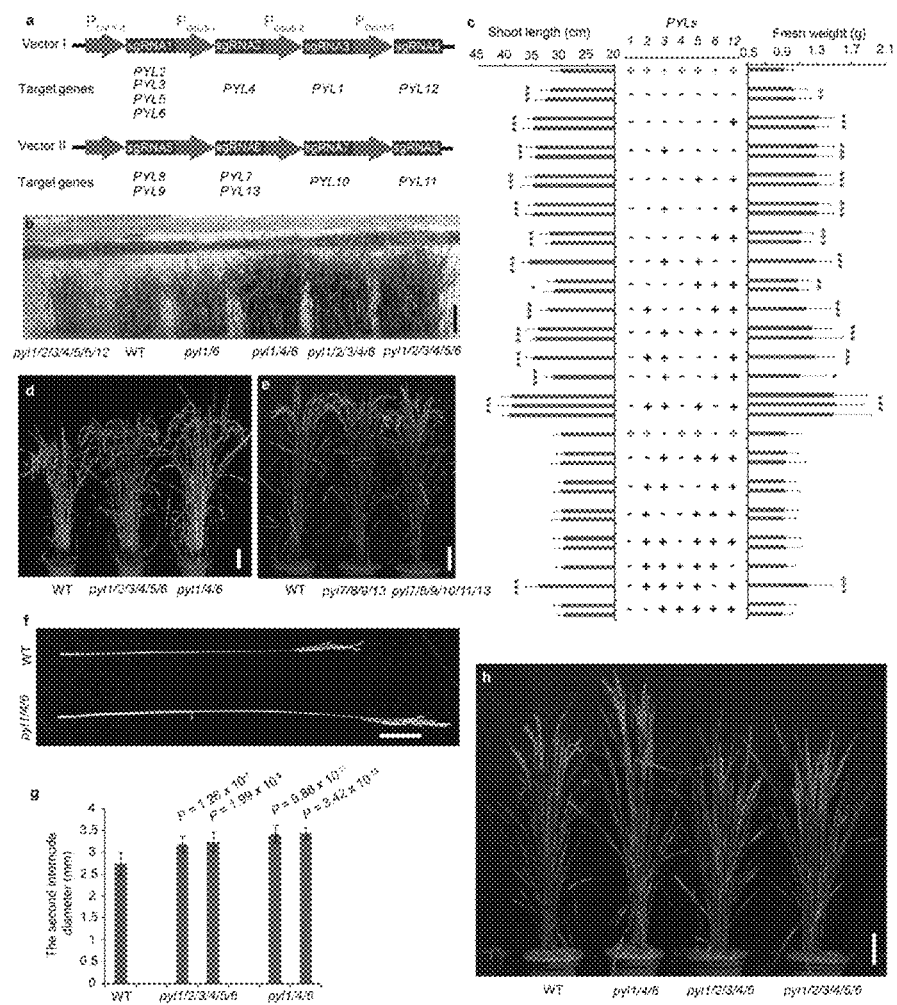
FIG. 2 shows that type I PYL gene mutations promote rice growth. a, rice PYL multiple gene knockout strategy. b, comparison of wild type and class I gene mutants at seedling stage. Scale, 10 cm. c, seedling length and fresh weight of wild-type and class I gene mutants. Each column represents an independent line. "+" refers to a wild-type gene, and "−" refers to a mutant gene. "*", the P value of the difference from the wild type is less than 0.001; "", the P value of the difference from the wild type is less than 0.01; "*", the P value of the difference from the wild type is less than 0.05. P-values were obtained using Student's t-test. d, comparison of wild-type, pyl 1/4/6 and pyl 1/2/3/4/5/6 on maturation stage. Scale, 10 cm. e, comparison of wild type, pyl 7/8/9/13 and pyl 7/8/9/10/11/13 during the filling stage. Scale, 10 cm. f, comparison of stems and ears of wild type and pyl 1/4/6. Scale, 10 cm. g, inverted internode diameter of wild type, pyl 1/4/6 and pyl 1/2/3/4/5/6. P-values were obtained using Student's t-test, showing a significance compared to wild type. h, comparison of wild type and class I gene mutants at heading stage. Scale, 10 cm.

We constructed two multi-gene targeted CRISPR/Cas9 vectors (the target site sequences were shown in Table 1), each of which targeted a cluster of genes on the rice PYL evolutionary tree. One vector targeted class I (group I) genes (PYL1-PYL6 and PYL12), and the other vector targeted class II (group II) genes (PYL7-PYL11 and PYL13) (FIGS. 1 and 2a). To knock out each PYL gene individually, we designed a specific target site for each target gene (Table 2) and constructed 13 single-gene targeted vectors.

Through the *Agrobacterium*-mediated transformation method, we transformed the vector into the rice variety Nipponbare. By the T2 generation, 153 class I gene mutant lines (A1-A108 from a multiple gene-knockout line and A109-A153 from a single gene-knockout line) and 84 class II gene mutant lines (B6-B51 from a multiple gene-knockout line, B52-B89 from a single gene-knockout line) were obtained (Annex 1). We did not obtain pyl7/8/9/10/11/13 mutants in the multi-gene editing line. In order to obtain pyl7/8/9/10/11/13, we hybridized pyl7/8/9/10/13 with pyl11 and identified 5 homozygous pyl7/8/9/10/11/13 in the F2 generation segregated populations (B1-B5). To ensure the stability of the genotype of the multi-gene editing line, we performed genotype identification on each generation of plants, and selected plants with stable genotype or without Cas9 for seed harvesting and phenotypic identification.

TABLE 1

Target site sequences for rice PYL multigene editing

| SEQ ID NO.: | target site sequence | target gene |
|---|---|---|
| 1 | TCAGCTTCCGCGTCGTCGGCGG | PYL2 PYL3 PYL5 PYL6 |
| 2 | GCGCACCACCGCTACGCCGTGGG | PYL1 |
| 3 | GGCGGCGGTAAGGCGTGCCCGG | PYL4 |
| 4 | GGATCATTGGAGGTGACCATAGG | PYL12 |
| 5 | AGCGGCAGGGAAGTTGCCAATGG | PYL8 PYL9 |
| 6 | CCGGGAGGAGGAGATGGAGTAC | PYL7 PYL13 |
| 7 | GGTGGCGGCTGGCGGACGAGAGG | PYL10 |
| 8 | GAGGAGGAGGTTGGAGGGTCGGG | PYL11 |

TABLE 2

Target site sequences for rice PYL single gene editing

| SEQ ID NO.: | target site sequence | target gene |
|---|---|---|
| 9 | GCGCACCACCGCTACGCCGTGGG | PYL1 |
| 10 | CCATCGTGCGCAGCTTCGGCAAC | PYL2 |
| 11 | GCGGGTTCGCCAACCCGCAGCGG | PYL3 |
| 12 | GTGCTCAGCTTCCGGATCGTCGG | PYL4 |
| 13 | GTGTGAGATAAGAGCGTGGTGGG | PYL5 |
| 14 | CCCTGGCATCCCGCACCAGCACC | PYL6 |
| 15 | CCGCCACGAAATCGGTAGCAACC | PYL7 |
| 16 | CCGGCAGTTCCACCGCCACGAGC | PYL8 |
| 17 | CCATTATAACAGAATTACTCATC | PYL9 |
| 18 | GGTGGCGGCTGGCGGACGAGAGG | PYL10 |
| 19 | GAGGAGGAGGTTGGAGGGTCGGG | PYL11 |
| 20 | GGATCATTGGAGGTGACCATAGG | PYL12 |
| 21 | CCACTTGGAGGTCATCGATGGCC | PYL13 |

Example 2. Rice PYL Subfamily Gene Mutation Promotes Rice Growth

Figure 3:
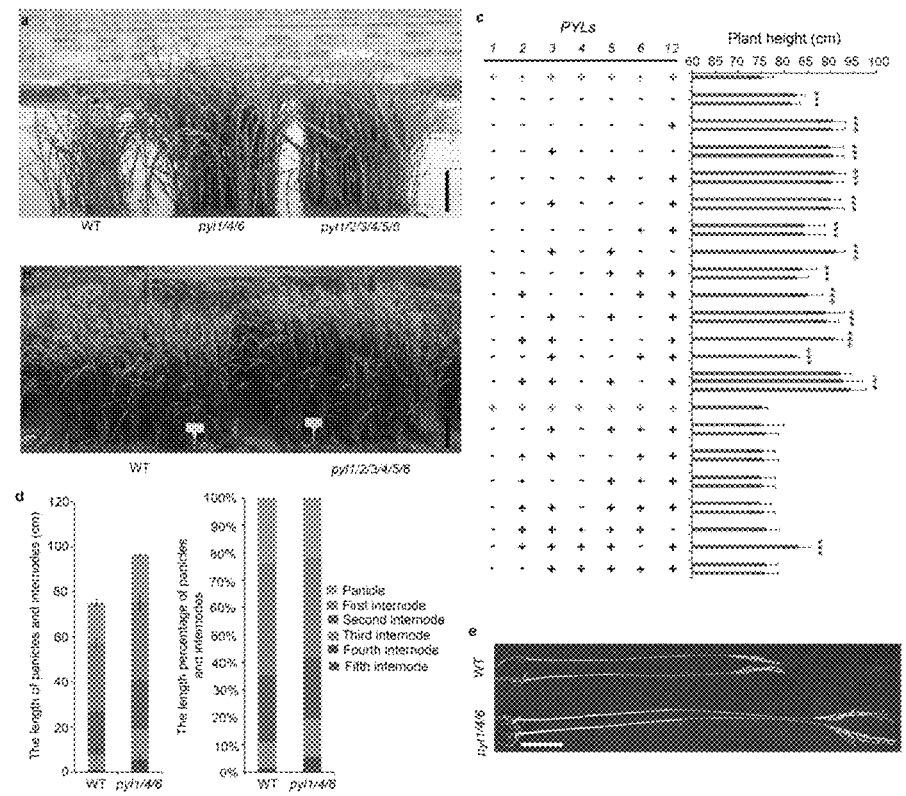
FIG. 3 shows the phenotypic identification of class I gene mutants. a, comparison of wild type, pyl 1/4/6 and pyl 1/2/3/4/5/6 at seedling stage. Scale, 10 cm. b, comparison of wild type and pyl 1/2/3/4/5/6 in the early stage of filling. Scale, 10 cm. c, the height of class I gene plants on maturation stage. Each column represents an independent line. "+" refers to a wild-type gene, and "−" refers to a mutant gene. "***", the P value of the difference from the wild type is less than 0.001. P-values were obtained using Student's t-test. d, comparison data of ear length and internode length between wild type and pyl1/4/6. The histogram on the left indicates the length and ear length of each internode; the histogram on the right indicates the ratio of ear length and internode length to plant height. e, comparison of ear length and internode length between wild type and pyl1/4/6. Scale, 10 cm.

The homozygous mutant materials obtained in this study were sown at the rice transgenic bases of the Institute of Plant Physiology and Ecology, Chinese Academy of Sciences in Shanghai and Lingshui Li Autonomous County, Hainan Province in mid-June and late-December every year. Field phenotypic observations revealed that there was no significant morphological difference between single-mutant lines or class II gene mutant lines and wild type of all genes (FIG. 2e), while many class I gene mutants showed better growth status than wild type (FIGS. 2b and 2d). At the seedling stage, from pyl1/6 to pyl1/2/3/4/5/6/12, most mutants grew more vigorous than the wild type and had stronger growth potential, especially the pyl1/4/6 triple mutants which had the best growth status (FIGS. 2b and 3a). In order to compare the growth differences between different mutation types and wild types, we calculated the plant height and fresh weight at the seedling stage (FIG. 2c). The statistical results show that pyl1/4/6 has the largest plant height and fresh weight, indicating that PYL1, PYL4 and PYL6 play a very important role in rice growth inhibition. Among the double mutants (pyl1/6, pyl1/4, pyl1/2, and pyl1/12), only pyl1/6 is larger than the wild type, and the others are not significantly different from the wild type. Among the triple mutants (pyl1/4/6, pyl1/2/4, pyl1/4/5 and pyl1/3/4), only pyl1/4/6 is larger than the wild type, and the others are not significantly different from the wild type. From the statistical data, it is also found that from triple mutants to seven mutants, pyl6-containing mutant lines grow better than other lines, suggesting that PYL6 plays a key role in rice growth inhibition (FIG. 2c).

On maturation stage, the class I mutants are continued to show stronger plant types than the wild type (FIG. 2d and FIG. 3b). To compare the differences between different mutants and wild-types at maturation stage, we measured the plant heights of various mutants. The plant height data on maturation stage has shown a similar pattern to that at the seedling stage, with pyl1/4/6 being the highest among all class I gene mutants and growing best (FIG. 2d and FIG. 3c).

Figure 4:
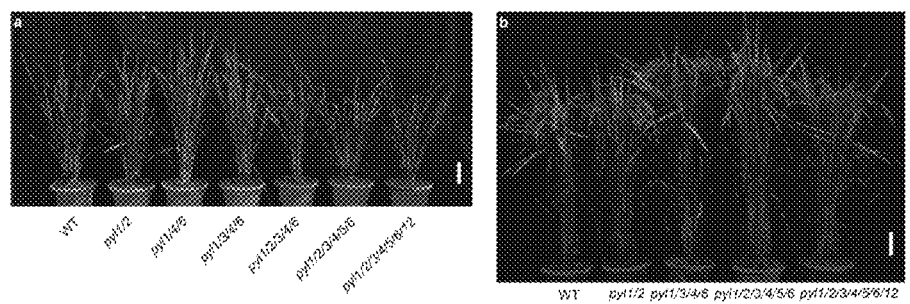
FIG. 4 shows the sensitivity of wild-type and class I gene mutants to hot weather. a, phenotypic comparison of wild-type and class I gene mutants undergoing the high-temperature climate of Shanghai in 2016. Scale, 10 cm. b, comparison of wild-type and type I gene mutants at the maturation stage undergoing the high-temperature climate of Shanghai in 2016. Scale, 10 cm.

In Shanghai in 2016, a high-temperature climate (the highest temperature at noon was about 40° C.) lasted at least two weeks from mid-July. Going through this high-temperature weather, we found that from four mutants to seven mutants, class I gene mutant materials showed different degrees of growth stagnation. The more mutations, the more severe the growth stagnation; during this period, pyl1/4/6 was still taller than the wild type (FIG. 4a). After heading stage, six and below mutants restored a larger growth phenotype, and seven mutants exhibited similar plant heights to the wild type (FIG. 4b). Class II gene mutants had no significant phenotypic difference from wild type during and after high temperature.

On the maturation stage, we also measured the stem diameter of the mutants. It was found that pyl1/2/3/4/5/6 and pyl1/4/6 had thicker stems compared to the wild type (FIGS. 2f and 2g). We also measured the stem node lengths of wild type and pyl1/4/6. Compared with the wild type, the ear length of pyl1/4/6 and each internode increased, especially the internode growth in the lower part increased significantly (FIGS. 3d and 3e).

The above phenotypic identification results indicate that type I PYL gene mutations can promote the rice growth, of which simultaneous mutations of PYL1, PYL4, and PYL6 have the best effect on growth promotion.

Example 3. Effect of Rice PYL Gene on Heading Stage

Heading stage affects the geographical distribution of rice and its adaptability to the season. In this study, we found that in the class I gene mutants, starting from the four mutants, the heading stage of the mutant lines was significantly delayed (FIG. 2h). Compared to the wild type, the heading stage of pyl1/2/3/4/5/6 and pyl1/2/3/4/5/6/12 was delayed for about 9 days, and that of pyl1/2/3/4/6 was delayed for about 7 days, that of pyl1/2/3/4 was delayed for about 5 days, and that of pyl1/4/6 was delayed for about 1 day. The heading stage of single mutant, double mutant and other triple mutants of class I gene was not significantly different from that of the wild type. There was no difference between the heading stage of the class II gene mutants and that of the wild type.

Example 4. Effect of Rice PYL Gene on Seed Dormancy

Figure 5:
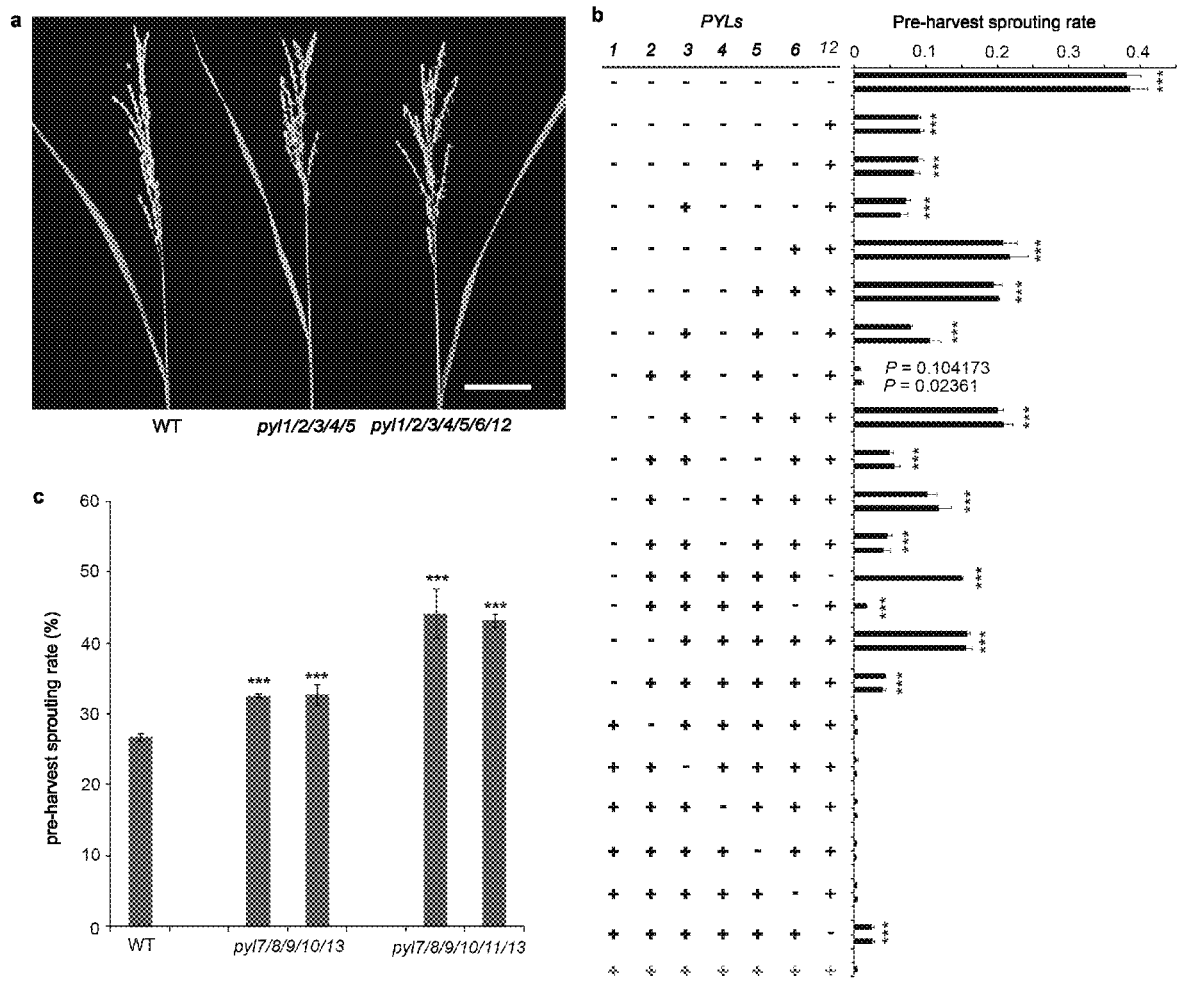
FIG. 5 shows the effect of rice PYL gene mutation on seed dormancy. a, PHS diagram of class I gene mutant seeds. Scale, 10 cm. b, pre-harvest sprouting (PHS) frequency of wild-type and class I gene mutant seeds. All the data are collected at the end of the pyl1/2/3/4/5/6/12 filling stage, and the statistical work is completed within one day. Each column represents an independent line, and each line counts all seeds of 3 plants. "+" refers to a wild-type gene, and "−" refers to a mutant gene. "*", the P value of the difference from the wild type is less than 0.001. "P=0.104173" and "P=0.02361" indicate that the P values of the difference from the wild type are 0.104173 and 0.02361, respectively. P-values are obtained using Student's t-test. c, PHS frequency of wild type and class II gene mutant seeds. PHS frequency is counted after seed harvest is delayed for about 25 days. Each column represents an independent line, and each line counts all seeds of 3 plants. "*", the P value of the difference from the wild type is less than 0.001.

ABA promotes seed dormancy, so that we investigated the dormancy of mutant seeds. Seed dormancy defects can cause seed germination before harvesting (pre-harvest sprouting, PHS). In class I gene mutants, we observed significant PHS (FIG. 5a). To compare the dormancy defects of different mutant seeds, we counted mutant and wild-type PHS in the field in 2016. The results show that among all class I gene mutants, pyl1/2/3/4/5/6/12 has the highest PHS frequency; among all single mutants, only pyl1 and pyl12 exhibit significantly higher PHS frequencies than wild type, indicating that PYL1 and PYL12 play a key role in seed dormancy (FIG. 5b). The statistics also show a surprising phenomenon. The PHS frequency of pyl1/6 is lower than that of pyl1, and the PHS frequency of pyl1/4/6 is lower than that of pyl1 and pyl1/4, indicating that PYL6 and other class I genes may have antagonistic effects on seed dormancy (FIG. 5b). In fact, from type I double mutants to seven mutants, pyl1/4/6 shows the lowest PHS frequency, and its PHS frequency is almost similar to the level of wild type (P values of two independent lines compared to wild type are 0.104173 and 0.02361) (FIG. 5b). In other years and seasons, no significant PHS on pyl1/4/6 was observed.

At normal harvest time, no significant PHS was observed on mutants of the class II gene, but when we delayed harvest time by about 25 days, pyl7/8/9/10/13 and pyl7/8/9/10/11/13 showed a slightly higher PHS frequency than the wild type (FIG. 5c), suggesting that rice class II genes also play a regulatory role in seed dormancy.

Example 5. Test of Pyl1/4/6 Mutation to Increase Rice Yield

Figure 6:
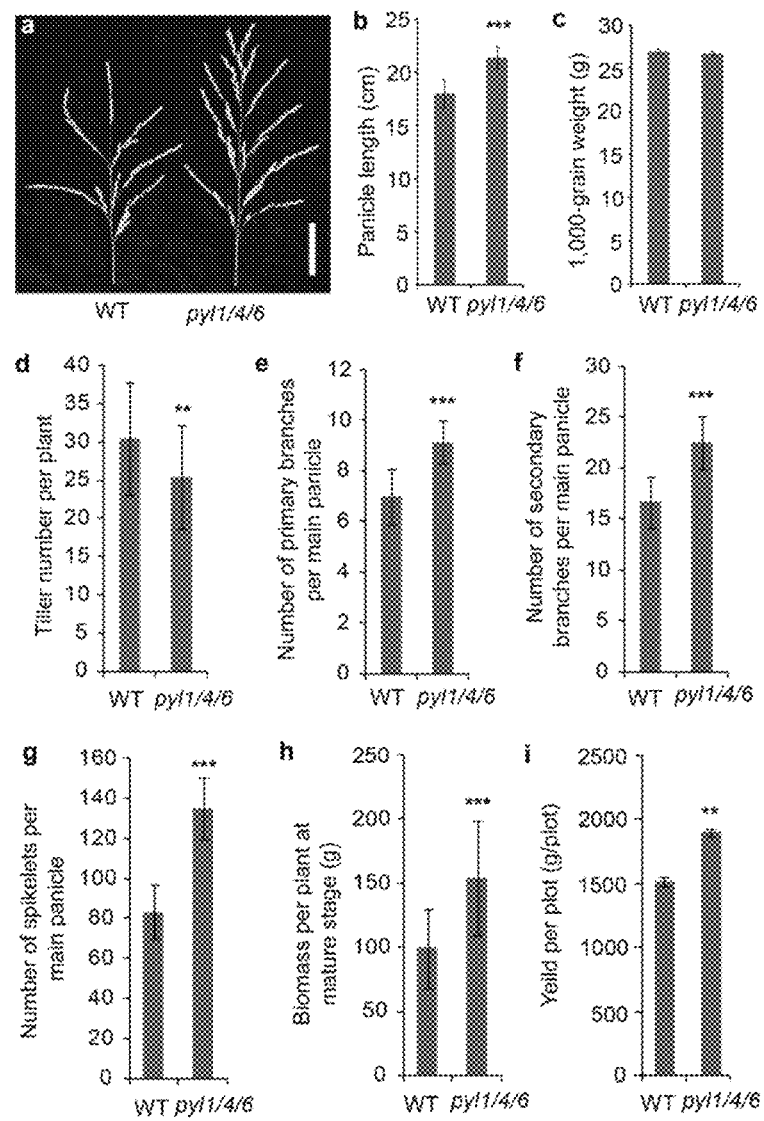
FIG. 6 shows analysis and testing of wild-type and pyl1/4/6 yield traits. a, comparison of wild type and pyl1/4/6 main spikes. Scale, 5 cm. b, main spike length data of wild-type and pyl1/4/6. "*", P value of difference from wild type is less than 0.001. c, Thousand Kernel Weight data of wild-type and pyl 1/4/6 seeds. d, statistics of tiller number of wild type and pyl 1/4/6. "", P value of difference from wild type is less than 0.01. e, primary branch data of primary spike of wild type and pyl 1/4/6. "*", P value of difference from wild type is less than 0.001. f, secondary branch data of main spike for wild type and pyl 1/4/6. "*", P value of difference from wild type is less than 0.001. g, number of florets in main spike of wild type and pyl 1/4/6. "*", P value of difference from wild type is less than 0.001. h, biomass data of wild-type and pyl 1/4/6 at maturation stage. "*", P value of difference from wild type is less than 0.001. i, plot yield test data of wild-type and mutant. "**", P value of difference from wild type is less than 0.01.

The above research results show that among many pyl mutants, pyl1/4/6 shows the best growth state, normal seed dormancy and heading stage. These results indicate that pyl1/4/6 may have potential application value. Therefore, we carefully investigated the agronomic traits of pyl1/4/6 and found that the seeding density of pyl1/4/6 panicles was not significantly different from that of wild type, but pyl1/4/6 had a longer ear type compared to wild type (FIGS. 6a and 6b). The number of primary and secondary branches of the main spike of pyl1/4/6 was significantly higher than that of the wild type (FIGS. 6e and 6f), so that the number of florets in the main spike was larger than that of the wild type (FIG. 6g). On maturation stage, the biomass of pyl1/4/6 increased by about 55.3% compared to the wild type, although its tiller number was significantly reduced compared to the wild type (FIGS. 6d and 6h). The Thousand Kernel Weight of pyl1/4/6 seeds was not significantly different from that of wild type (FIG. 6c, P=0.230034).

Figure 7:
FIG. 7 shows the effect chart of the Shanghai pyl 1/4/6 yield test in 2016.

Next, we conducted a production test in a small field (FIG. 7). Wild-type and mutants were planted in small blocks arranged alternately. In each small block, the plant spacing was fixed at 15 cm, with 12 rows and 12 columns. Each material was set to repeat in 3 plots. 2016 Shanghai production test results show that pyl1/4/6 increases grain yield by 25% compared to wild type (wild-type small block yield, 1522.4±36.3 g; pyl1/4/6 small block yield, 1899.8±30.8 g). In 2017, Hainan's production test results show that the yield of pyl1/4/6 has increased by 31% compared with the wild type (the yield of small blocks of wild type, 1317.5±25.7 g; the yield of small blocks of pyl1/4/6, 1727.1±34.9 g).

The above results show that the pyl1/4/6 mutation can significantly increase rice yield.

The invention claimed is:

1. A method for producing transgenic rice plant cells, a transgenic rice plant tissue, transgenic rice plant, or transgenic seed or grain derived therefrom, comprising the steps:
   (i) reducing or eliminating rice endogenous Pyrabactin Resistant 1-Like 1 (PYL1) and Pyrabactin Resistant 1-Like 6 (PYL6) gene expression by CRISPR technology to reduce or eliminate expression of the rice endogenous PYL1 and PYL6 genes in rice cells, wherein the CRISPR technology comprises transforming said rice cells with a recombinant CRISPR/Cas9 vector targeted to said rice endogenous PYL1 and PYL6 genes to reduce or eliminate expression of said rice endogenous PYL1 and PYL6 genes thereby producing transformed rice cells;
   (ii) regenerating said transformed rice cells of step (i) into a regenerated transformed rice plant and performing a trait testing on the regenerated transformed rice plant, wherein the trait is selected from the group consisting of plant height, plant yield and plant biomass; and
   (iii) based on the results of the trait testing from step (ii), selecting a regenerated transformed rice plant with an improved plant trait characteristic, wherein the improved plant trait characteristic comprises increased plant height, increased plant yield or increased plant biomass, and wherein the transgenic rice plant cells, said transgenic rice plant tissue, transgenic rice plant, or transgenic rice seed or rice grain derived therefrom is obtained from the selected regenerated transformed rice plant with the improved plant trait characteristic.

2. The method of claim 1, wherein the CRISPR technology comprises gene editing with multiple sgRNA-mediated Cas9 nucleases targeted to said rice endogenous PYL1 and PYL6 genes.

3. A method for producing transgenic rice grain, comprising the steps of:
   (a) planting a transgenic rice crop of said selected transgenic rice plants with reduced or eliminated rice endogenous PYL1 and PYL6 gene expression, and having said improved plant trait characteristics according to claim 1; and
   (b) harvesting transgenic rice grain from the transgenic rice crop.

4. The method of claim 1, wherein said recombinant CRISPR/Cas9 vector is further targeted to rice endogenous PYL4 gene to reduce or eliminate expression of said rice endogenous PYL4 gene.

* * * * *